(12) United States Patent
Parsons (10) Patent No.: US 11,684,373 B2
(45) Date of Patent: Jun. 27, 2023

(54) LIGHTWEIGHT TOURNIQUET

(71) Applicant: Recon Medical, LLC, Redding, CA (US)

(72) Inventor: Derek Parsons, Redding, CA (US)

(*) Notice: Subject to any disclaimer, the term of this patent is extended or adjusted under 35 U.S.C. 154(b) by 159 days.

(21) Appl. No.: 17/023,359

(22) Filed: Sep. 16, 2020

(65) Prior Publication Data

US 2021/0000482 A1    Jan. 7, 2021

(51) Int. Cl.
*A61B 17/132* (2006.01)

(52) U.S. Cl.
CPC .................. *A61B 17/1327* (2013.01)

(58) Field of Classification Search
CPC .............. A61B 17/132; A61B 17/1322; A61B 17/1327
See application file for complete search history.

(56) References Cited

U.S. PATENT DOCUMENTS

| | | |
|---|---|---|
| 104,683 A | 6/1870 | Alexander |
| 341,127 A | 5/1886 | Bretzfield |
| 486,374 A | 11/1892 | Greenwood et al. |
| 631,659 A | 8/1899 | Orewiler |
| 840,878 A | 1/1907 | Stenzy |
| 871,981 A | 11/1907 | Blum |
| 892,963 A | 7/1908 | Lebowitz |
| 1,147,955 A | 7/1915 | Langhammer |
| 1,232,546 A | 7/1917 | Holden |
| 1,299,734 A | 4/1919 | Kerngood |
| 1,325,948 A | 12/1919 | Lebowitz |
| 1,423,639 A | 7/1922 | Anderson |
| D64,754 S | 5/1924 | Kline |
| 1,653,852 A | 12/1927 | Hatheway |
| 1,679,306 A | 7/1928 | Hirsh |
| D78,590 S | 5/1929 | Shields |
| 1,820,578 A | 8/1931 | Mosgrove |
| 1,887,614 A | 11/1932 | Louis |
| 1,934,951 A | 11/1933 | Schaefer |
| 1,987,469 A | 1/1935 | Devendor et al. |
| 2,062,734 A | 12/1936 | Troendly |
| 2,084,412 A | 6/1937 | Schaefer |
| 2,189,574 A | 2/1940 | Anderson |
| D121,618 S | 7/1940 | Reiter |
| D125,083 S | 2/1941 | Dickson |
| D138,185 S | 7/1944 | Reiter |
| 2,480,430 A | 8/1949 | Nugent |
| 3,156,243 A | 11/1964 | Sculley |
| 3,760,466 A | 9/1973 | Leblanc |
| 3,786,816 A | 1/1974 | Wolvek |
| 3,869,763 A | 3/1975 | Senk et al. |

(Continued)

OTHER PUBLICATIONS

Amazon—Eyocean tourniquet—Reviewed on Aug. 6, 2018.
Gistgear—"Gistgear the essential guide to the best gear"—first found on Jun. 22, 2018.

*Primary Examiner* — Ryan J. Severson
(74) *Attorney, Agent, or Firm* — Michael Scheinberg; Scheinberg $ Associates, PC (57) ABSTRACT

A tourniquet is described that includes an outer strap that runs from a first end to a second end having a buckle. An inner strap is routed within the outer strap over a portion of its length and runs through a windlass, which is used to tighten the tourniquet. The inner strap is secured to the outer strap at a position spaced away from the first end of the outer strap and is also secured to the buckle.

22 Claims, 8 Drawing Sheets

(56) References Cited

U.S. PATENT DOCUMENTS

| | | |
|---|---|---|
| 4,023,826 A | 5/1977 | Kokubo et al. |
| 4,561,437 A | 12/1985 | Kirchner |
| D287,067 S | 12/1986 | Kasai |
| D303,456 S | 9/1989 | Selisky |
| D308,166 S | 5/1990 | Weckman |
| D328,044 S | 7/1992 | Murai |
| D328,045 S | 7/1992 | Matoba |
| D352,254 S | 11/1994 | Prosser |
| D352,255 S | 11/1994 | Prosser |
| D364,833 S | 12/1995 | Matoba |
| D381,427 S | 7/1997 | Marrero |
| D386,110 S | 11/1997 | Hetrick et al. |
| D394,024 S | 5/1998 | Johnson, I |
| D411,485 S | 6/1999 | Dreyfus et al. |
| D413,281 S | 8/1999 | Uehara |
| D427,547 S | 7/2000 | Yoshiguchi |
| 6,149,618 A | 11/2000 | Sato |
| D436,057 S | 1/2001 | Hotta |
| 6,217,601 B1 | 4/2001 | Chao |
| D446,162 S | 8/2001 | Kung |
| D450,263 S | 11/2001 | Striebel |
| D452,185 S | 12/2001 | Yoshiguchi |
| D456,309 S | 4/2002 | Yoshiguchi |
| D467,838 S | 12/2002 | Yoshiguchi |
| D471,132 S | 3/2003 | Murata |
| 6,622,348 B1 | 9/2003 | Buscart |
| D483,294 S | 12/2003 | Uehara |
| D486,093 S | 2/2004 | Tobergte |
| D491,103 S | 6/2004 | Uehara et al. |
| D505,094 S | 5/2005 | Matoba et al. |
| D507,763 S | 7/2005 | Kaneko et al. |
| D507,990 S | 8/2005 | Yoshiguchi |
| D509,769 S | 9/2005 | Krauss |
| D520,908 S | 5/2006 | Haymond |
| D536,280 S | 2/2007 | Wemmer |
| D538,198 S | 3/2007 | Wemmer |
| D545,243 S | 6/2007 | Gracer et al. |
| D562,729 S | 2/2008 | Hitchcock |
| D563,270 S | 3/2008 | Zeng et al. |
| D568,786 S | 5/2008 | Yang et al. |
| D576,077 S | 9/2008 | Yoshiguchi |
| D586,259 S | 2/2009 | Kelleghan |
| D586,692 S | 2/2009 | Nykoluk |
| D610,946 S | 3/2010 | Harada |
| D617,234 S | 6/2010 | Chan |
| D620,837 S | 8/2010 | Schiebl |
| D623,556 S | 9/2010 | Pontaoe |
| 7,842,067 B2 | 11/2010 | Esposito |
| D628,515 S | 12/2010 | Schiebl |
| 7,892,253 B2 | 2/2011 | Esposito et al. |
| D649,087 S | 11/2011 | Harada |
| D649,642 S | 11/2011 | Johnson |
| D649,907 S | 12/2011 | Kataguchi |
| D653,169 S | 1/2012 | Lo |
| 8,343,182 B2 * | 1/2013 | Kirkham .............. A61B 17/1322 606/203 |
| D682,155 S | 5/2013 | Parsons |
| D689,608 S | 9/2013 | Kerstein et al. |
| D703,096 S | 4/2014 | Kelleghan |
| D712,306 S | 9/2014 | Fildan et al. |
| D713,759 S | 9/2014 | Guney et al. |
| 8,888,807 B2 | 11/2014 | Esposito |
| D729,689 S | 5/2015 | Kelleghan |
| D733,305 S | 6/2015 | Miyashita |
| D786,735 S | 5/2017 | Koreishi et al. |
| D791,951 S | 7/2017 | Henderson |
| D810,300 S | 2/2018 | Parsons |
| D812,170 S | 3/2018 | Henderson |
| D823,466 S | 7/2018 | Marogil |
| D823,717 S | 7/2018 | Ho |
| D824,522 S | 7/2018 | Brown |
| 10,016,203 B2 | 7/2018 | Esposito |
| D825,752 S | 8/2018 | Dimino et al. |
| D826,408 S | 8/2018 | Harder |
| D828,564 S | 9/2018 | Harder |
| D840,869 S | 2/2019 | Koreishi |
| D840,870 S | 2/2019 | Koreishi |
| 10,194,917 B1 * | 2/2019 | Carson .............. A61B 17/1327 |
| D847,016 S | 4/2019 | Stringham |
| D855,186 S | 7/2019 | Donald |
| D858,774 S | 9/2019 | Parsons |
| D860,858 S | 9/2019 | Evans et al. |
| D891,614 S | 7/2020 | Dimino |
| 10,765,437 B1 * | 9/2020 | Antonio ............. A61B 17/1325 |
| D906,168 S * | 12/2020 | Parsons ........................ D11/218 |
| D935,618 S * | 11/2021 | Parsons ........................ D24/171 |
| D938,593 S * | 12/2021 | Parsons ........................ D24/169 |
| 2003/0028215 A1 | 2/2003 | Brooks |
| 2005/0240217 A1 | 10/2005 | Jennifer et al. |
| 2005/0273134 A1 * | 12/2005 | Esposito ............. A61B 17/1327 606/203 |
| 2007/0005107 A1 * | 1/2007 | Janota ................ A61B 17/1322 606/203 |
| 2007/0163088 A1 | 7/2007 | Gracer et al. |
| 2008/0281351 A1 | 11/2008 | Croushorn et al. |
| 2009/0005804 A1 | 1/2009 | Esposito et al. |
| 2010/0057120 A1 | 3/2010 | Kirkham |
| 2010/0170065 A1 | 7/2010 | Paik |
| 2010/0312271 A1 | 12/2010 | Chao |
| 2011/0178546 A1 | 7/2011 | Johnson et al. |
| 2011/0239416 A1 | 10/2011 | Shinya et al. |
| 2011/0270299 A1 | 11/2011 | Rose et al. |
| 2011/0307004 A1 | 12/2011 | Johnson et al. |
| 2012/0071917 A1 | 3/2012 | McDonald et al. |
| 2012/0215254 A1 | 8/2012 | Brub |
| 2013/0110019 A1 | 5/2013 | Hopman et al. |
| 2014/0214054 A1 | 7/2014 | Foerster et al. |
| 2015/0094756 A1 | 4/2015 | Kosiorek et al. |
| 2015/0257767 A1 * | 9/2015 | Henderson ......... A61B 17/1327 441/75 |
| 2016/0345981 A1 * | 12/2016 | Demas ............... A61B 17/1327 |
| 2017/0032698 A1 | 2/2017 | Bronson et al. |
| 2017/0035440 A1 | 2/2017 | Hopman et al. |
| 2018/0153557 A1 * | 6/2018 | Dimino .............. A61B 17/1327 |
| 2018/0193032 A1 * | 7/2018 | Haeussinger ....... A61B 17/1325 |
| 2018/0228497 A1 | 8/2018 | Dimino et al. |
| 2018/0317935 A1 | 11/2018 | Engwall |
| 2018/0353189 A1 | 12/2018 | Goolsby et al. |
| 2020/0367909 A1 * | 11/2020 | Rankins, III ....... A61B 17/1325 |
| 2021/0000482 A1 * | 1/2021 | Parsons ............. A61B 17/1322 |
| 2021/0153873 A1 * | 5/2021 | Peterson ............ A61B 17/1322 |
| 2022/0047273 A1 * | 2/2022 | Parsons ............. A61B 17/1322 |

* cited by examiner

LIGHTWEIGHT TOURNIQUET

TECHNICAL FIELD OF THE INVENTION

The present invention relates to tourniquets, and in particular to light weight tourniquets.

BACKGROUND OF THE INVENTION

A tourniquet is a constricting band placed around a limb and tightened to eliminate arterial flow past the device to prevent bleeding. Simply tying a constricting band or material tightly around a limb rarely provides enough pressure to stop arterial blood flow. To block arterial flow requires a mechanical advantage to tighten the constricting band. A windlass or twist stick is conventionally used to tighten the constricting band or material to stop the arterial flow.

Arterial blood flow (from the heart to extremities) into a limb is usually at a high-pressure and requires high pressure deep in the limb to occlude or stop the arterial flow. Venous blood flow, that is, blood flowing from a limb and back to the heart, is usually at a lower pressure and therefor requires less pressure than arterial flow to stop.

Material wrapped tightly around a limb, but without a "twist stick" or windlass to apply mechanical tension to the material, is a venous (low pressure) constricting band at best. Although arterial flow still occurs when material is merely wrapped tightly around a limb, which moves blood into the injured limb, the venous system is occluded or mostly occluded and cannot return blood to the body. The blood that is flowing past the material wrapping through the artery will flow into the limb and will exit the limb through the wound in the limb, and thus out of body, resulting in blood loss. For wounded patients, that is detrimental if not fatal, but for taking blood samples that is desirable, where the phlebotomist places a "venous constricting band" around an arm to occlude the venous system which engorges the veins in the limb, making it easier to draw blood from enlarged veins. Thus, tourniquets without windlasses are venous constricting bands because windlasses are necessary to tighten the constricting band to prevent hemorrhaging through the wound.

Tourniquets are typically used as an emergency measure in settings that are far from medical facilities. Because tourniquets are carried in the field, they are preferably as light as possible, consistent with being sufficiently strong to stop arterial blood flow and not fall apart under the strain of use. A problem with some prior art light weight tourniquets is that they are insufficiently strong, and can unravel under pressure, particularly when used on a large limb, such as the limb of an obese person.

SUMMARY OF THE INVENTION

An object of the invention is to provide a method and apparatus for an improved tourniquet.

A tourniquet includes an inner strap and an outer strap. The outer strap has a first end and a second end with a buckle. The inner strap extends from a point that is spaced away from the first end, passes through a windlass, and is knotted around the buckle.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

Figure 1:
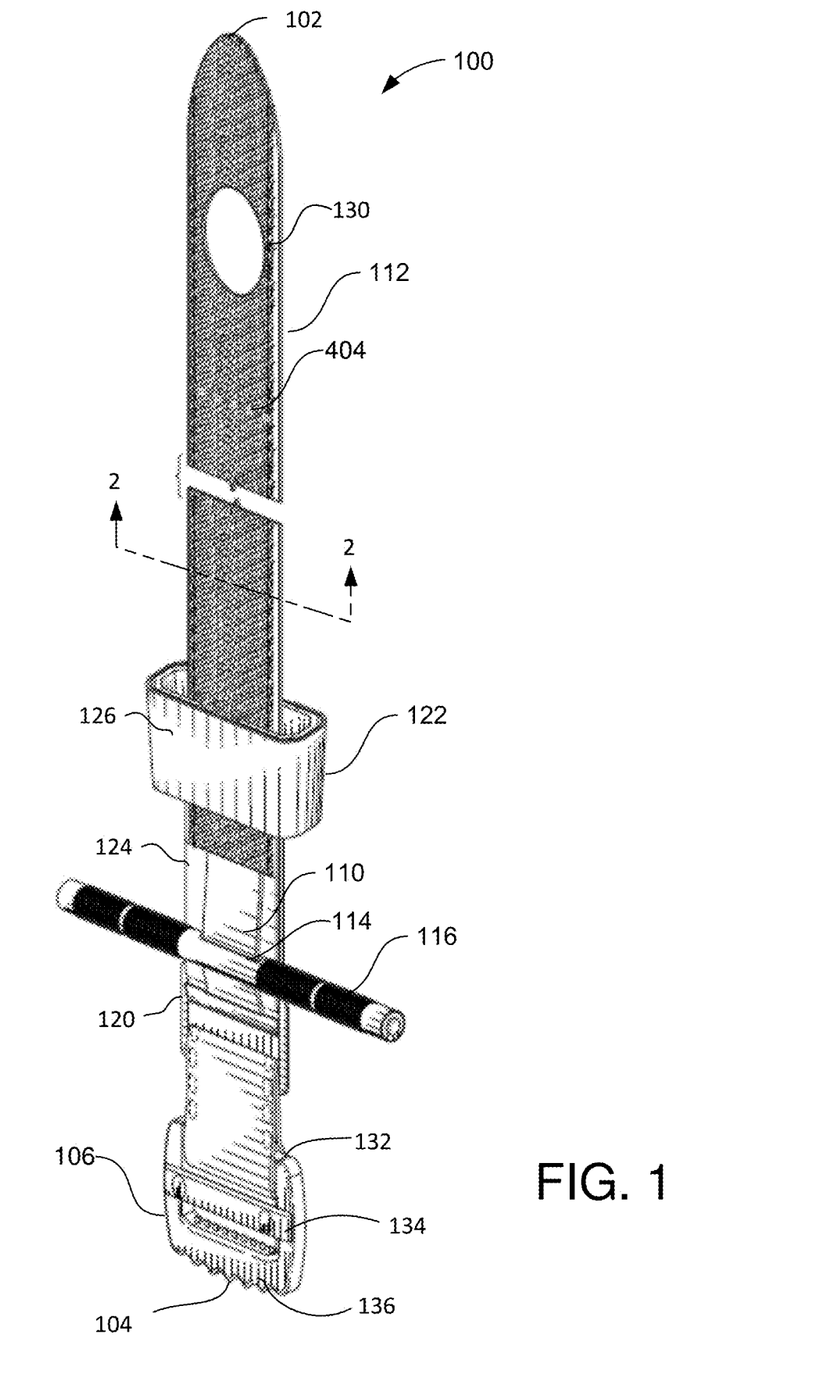
FIG. 1 is an isometric view of a tourniquet.
Figure 2:
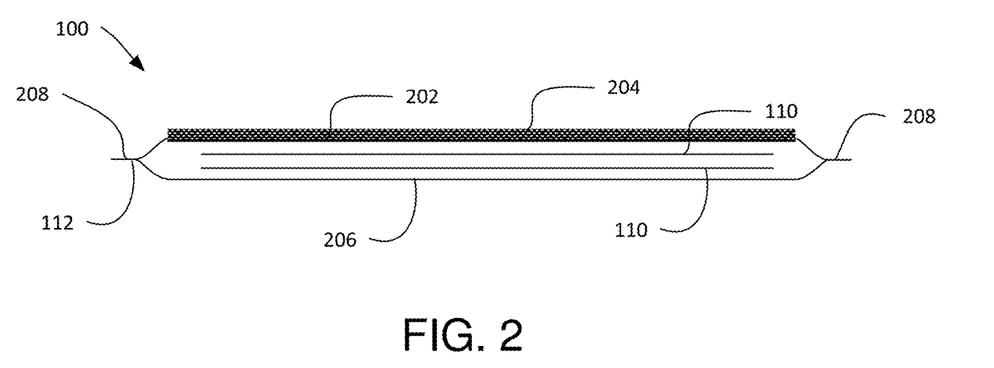
FIG. 2 is a cross sectional view taken along the lines 2-2 of FIG. 1.

FIG. 1 shows an embodiment of a tourniquet 100, having a first end 102 and a second end 104 at which a buckle 106 is secured. FIG. 2 shows a cross section of tourniquet 100 taken along lines 2-2. Tourniquet 100 includes an outer strap 112 that comprises an upper layer 202 covered with a layer of hook and loop fasteners 204 and a lower layer 206. Upper layer 202 and lower layer 206 are connected together at their edges 208, for example, by stitching or welding, to form a tube. While lower layer 206 and upper layer 202 are referred to as two different layers, it will be understood that lower layer 206 and upper layer 202 can be formed in some parts of their length by the same piece of fabric that is folded over itself, for example, lengthwise, after being routed longitudinally along the tourniquet or transversely. Longitudinally refers to either direction along a line running from end 102 to end 104. Outer strap 112 need not be continuous from end 102 to buckle 106. For example, upper layer 202 can be discontinuous, that is, can stop and restart after a gap, as in an embodiment described below. Over a portion of the length of tourniquet 100, an inner strap 110 runs within the tube created by upper layer 202 and lower layer 206.

Figure 3:
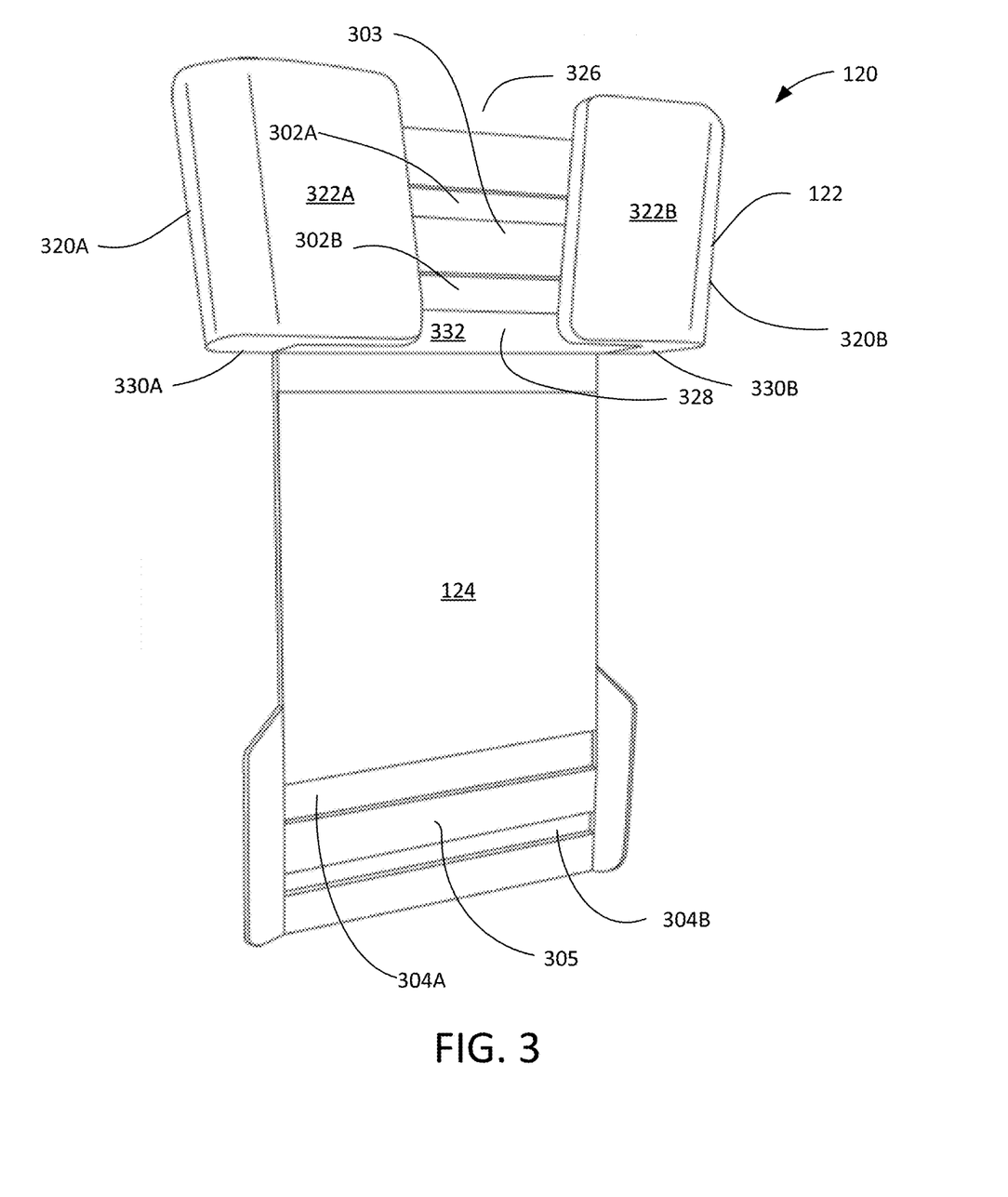
FIG. 3 is an isometric view of a windlass platform of the tourniquet of FIG. 1, the windlass platform shown separated from the rest of the tourniquet.

A windlass platform 120 includes a windlass retainer clip 122 and a flat region 124. A windlass strap 126 including hook and loop fasteners wraps over the top opening of windlass clip 122 to retain windlass 116 within windlass clip 122 after the windlass has been twisted to tighten inner strap 110. Windlass platform 120 is shown in more detail with the straps removed in FIG. 3. As seen in FIG. 3, windlass platform 120 has a first set of slits 302A and 302B separate by a first cross bar 303 and a second set of slits 304A and 304B separated by a second cross bar 305. Windlass clip 122 extends above slits 302A and 302B. Windlass clip 122 includes side portions 320A and 320B (only edges 320B are visible in FIG. 3) and top portions 322A and 322B. Top portions 322A and 322B are both substantially parallel to flat region 124. Side portions 320A and 320B can be straight or curved. In some embodiments, side portions 320A and 320B are composed of 3 intersecting straight portions forming ½ of an octagon. Side portions 320A and 320B are angled inward in the direction of buckle 106. That is, a rear windlass clip opening 326 is wider than a front windlass clip opening 328. Windlass clip 122 includes a rib 330A that connects the top portion 322A, the side portion 320A, and a bottom portion 332 at the front opening 328 and a rib 330B that connects the top portion 322B, the side portion 320B, and bottom portion 332 at the front opening 328. Ribs 330A and 330B provide additional mechanical strength to windlass clip 122 allowing it to better resist the torque from the tightened windlass. The routing of the inner strap 110 and of outer strap 112 are shown schematically in FIG. 4.

Figure 5:
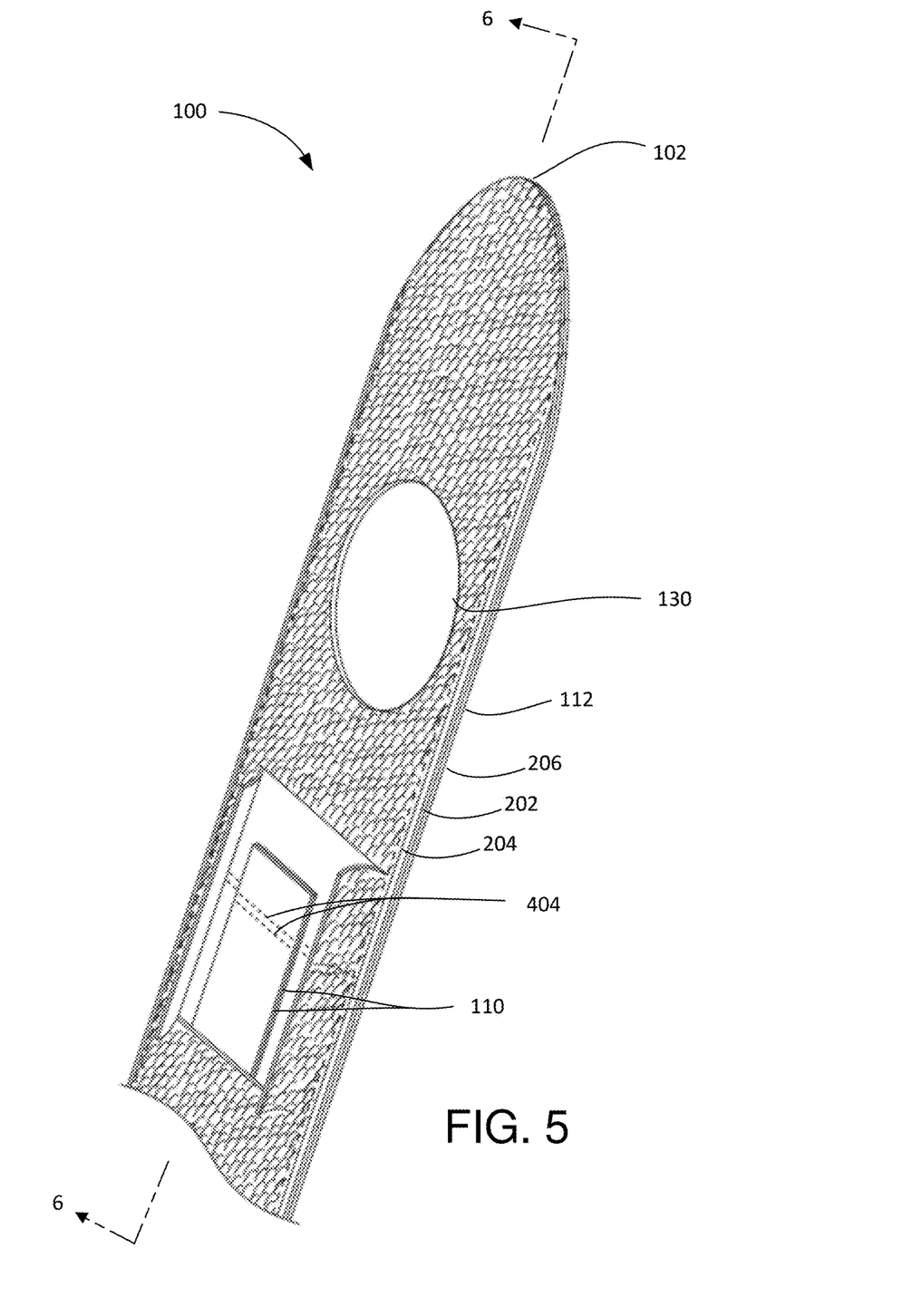
FIG. 5 is an enlarged view of a portion of the tourniquet of FIG. 1.

Outer strap 112 terminates at end 102 in a paraboloid or bullet shape. FIG. 5 shows an enlarged view of a portion of the tourniquet 100 including end 102. FIG. 5 shows a portion of outer layer 112 is shown cut and folded back to expose inner strap 110 where it is secured to outer strap 112. Upper layer 202 is shown cut and folded back for illustration purposed only, and outer strap 112 is actually continuous and intact at that portion.

Figure 6:
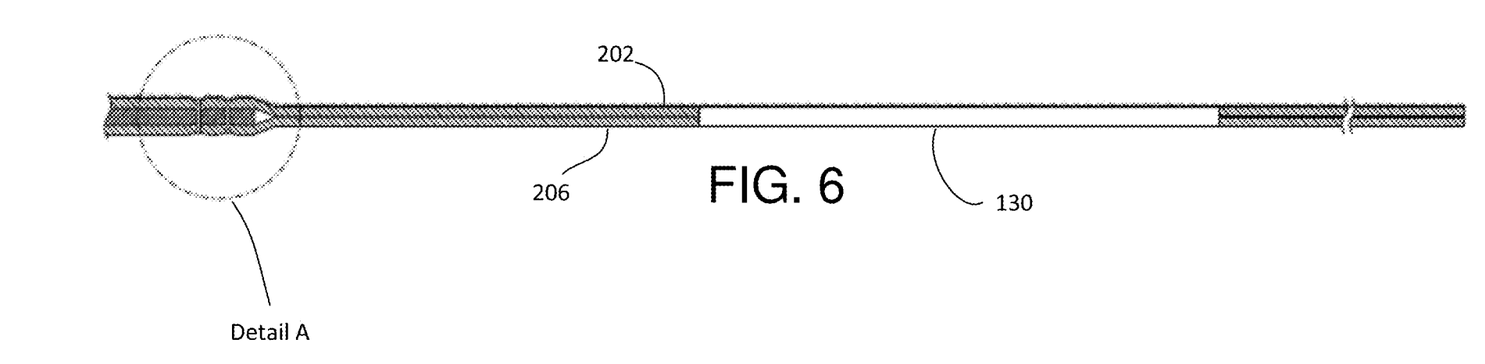
FIG. 6 is a cross sectional view of the tourniquet of FIG. 5, taken along lines 6-6.
Figure 6A:
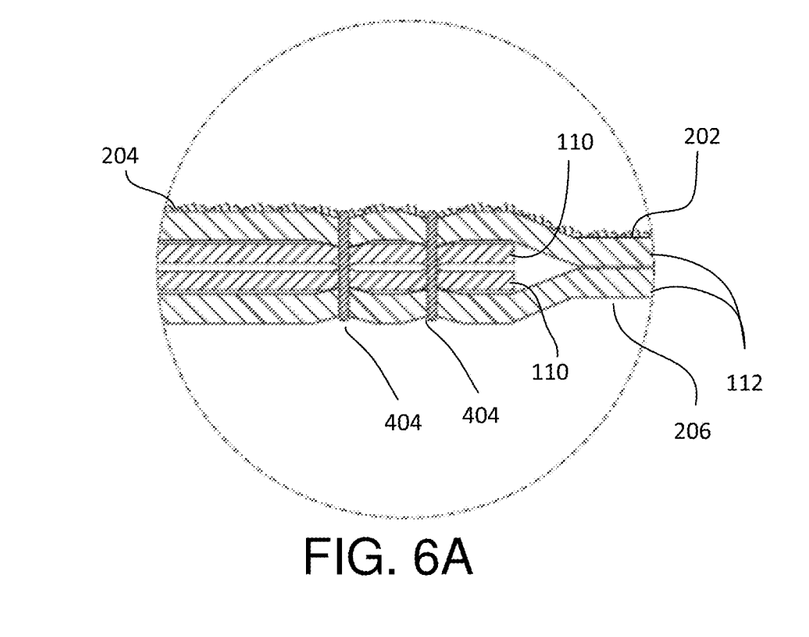
FIG. 6A is a detail view of a portion of the tourniquet of FIG. 6.

FIG. 6 is a cross section view taken along the line 6-6 of FIG. 5. FIG. 6A is a detail view of a portion of FIG. 6 where the ends of inner strap 110 are secured to outer strap 112 by two row of stitching 404. Stitching 404 runs transverse to the longitudinal axis of tourniquet 100, preferably over most of the width of outer strap 112, to spread the tension over a greater linear dimension. Tension in strap 110 is transferred to strap 112 by stitching 404 over a larger region of strap 112 than the stress transfer region in the prior art, in which the transferred stress is concentrated at the tip of end 102. In the prior art, securing inner strap 110 at end 102 tends to lead to failure of the tourniquet when tension is applied to inner strap 110 to constrict tourniquet 100 around a limb, particularly a large limb, such as the limb of an obese individual.

The two rows of stitches 404 are separated by a small distance, preferably between ¹⁄₁₆" and ¼", preferably about ⅛", to spread the tension from inner strap 110 over an area of outer strap 112. Alternatively, a single line of stitches or three or more lines of stitching can be used.

Thumb hole 130 is cut in outer strap 112 with the center of the thumb hole about 2" in from the end 102. As shown in FIG. 5, both ends of inner strap 110 extend from a region on the side opposite of the thumbhole from end 102. In one embodiment, inner strap 110 begins at about 3½ to 4 inches away from end 102. That is, inner strap 110 does not extend to end 102. A small length of inner strap 110 extends unsecured beyond stitching 404 toward thumb hole 130.

Figure 4:
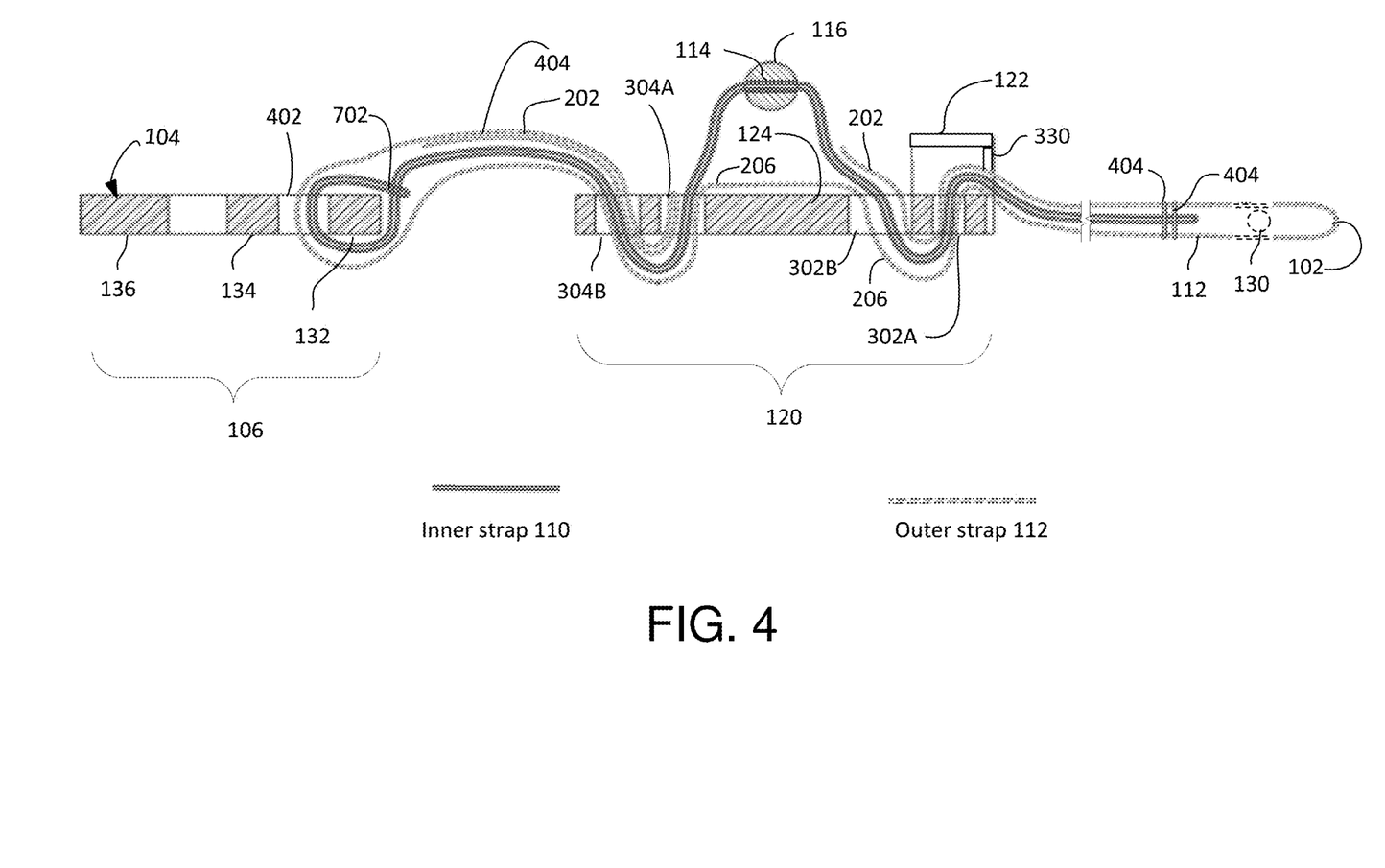
FIG. 4 is a schematic of the routing of the straps of the tourniquet of FIG. 1.

FIG. 4 shows outer strap 112, with inner strap 110 within, is routed through slit 302A of windlass platform 120 from above ("above" platform 120 meaning the side to which windlass clip 122 extends) and then back up to the top side of windlass platform 120 through slit 302B. Above slit 302B, upper layer 202 stops and lower layer 206 extends across flat portion 124. As upper layer 202 stops, inner strap 110 exits the tube formed by upper layer 202 and lower layer 206 and passes a through slot 114 in a windlass 116.

Top layer 202 restarts at slit 304A, going below restraining platform 120, along with bottom lawyer 206 and inner strap 110 and returning through slit 304B to a location above platform 120, with inner strap 110 being positioned within the tube formed by upper layer 202 and lower layer 206. As shown in FIG. 4, top portion 202 of outer strap 112 doubles back on itself through slits 304A and 304B, thereby avoiding a loose end where top portion 202 restarts after flat portion 124.

FIG. 4 shows that buckle 106 includes three cross-bars: a rear crossbar 132, a center cross bar 134, and a front cross bar 136. Inner strap 110 continues, surrounded by outer strap 112, and is knotted around rear crossbar 132.

Figure 7:
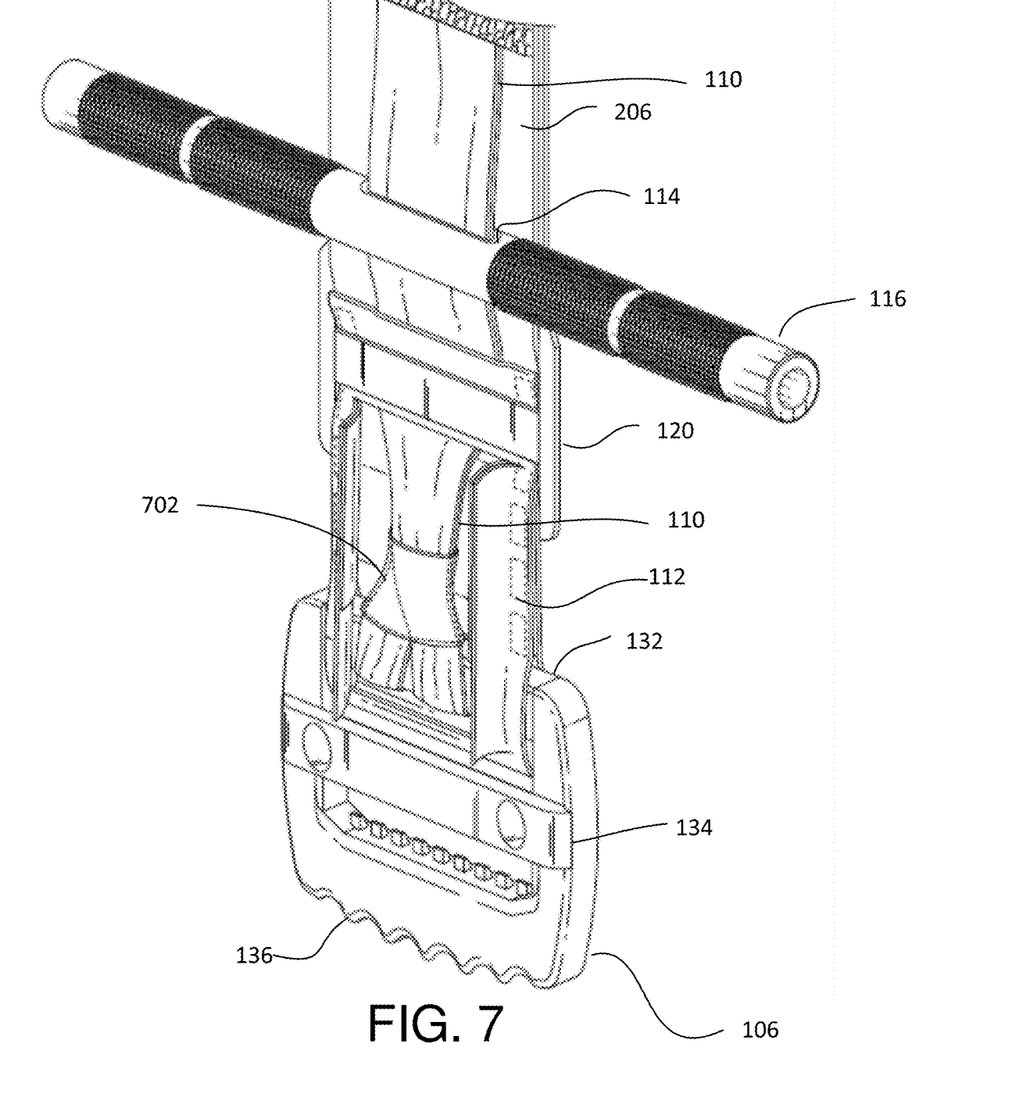
FIG. 7 is an isometric view showing a portion near the buckle of the tourniquet of FIG. 1, the tourniquet shown with a portion of the outer strap cut and folded away to expose a portion of inner strap at the buckle.

FIG. 7 shows an enlarged view of inner strap 110 and outer strap 112 at buckle 106, with the upper layer of outer strap 112 cut and folded away to expose inner strap. It will be understood that in an actual tourniquet 100, outer strap 112 is not cut open and inner strap is not visible. The binding at the edge of outer strap 112, which binds upper layer 202 and lower layer 206, is interrupted to allow rear cross bar 132 to pass through outer strap 112 between upper layer 202 and lower layer 206. As can be seen in FIG. 4, what are referred to herein as upper layer 202 and lower layer 206 are part of the same piece of fabric that surrounds the cow hitch knot 702 created by inner strap 110 and loops back onto itself at rear cross bar 132 to create two layers.

Inner strap 110 is shown connected by a knot 702 around cross bar 132. Any type of knot can be used. A "cow hitch" knot is shown. A cow hitch knot has the advantage of being simple and not bulky. The cow hitch is a "slip knot" that tightens as the inner strap is pulled in tension during application. There is no gap between the cross bar 132 and inner strap 110 as it is knotted around cross bar 132.

In the embodiment shown, inner strap 110 is routed from just before stitching 404, through slot 114 in windlass 116, is knotted around rear cross bar 132, and returns following the same routing back to just beyond stitching 404. An advantage of using a knot at buckle 136, as opposed to just looping around cross bar 136 without a knot, is that if one leg of inner strap 110 becomes loose at stitching 404, inner strap 110 will not merely slip around cross bar 132 under tension and come loose, but the other leg of inner strap 110 will remain secured to rear cross bar 132 and support tension in the tourniquet. In some embodiments, inner strap can extend from stitching 404 and be secured at buckle 106 without returning back to stitching 404. That is, rather than having two lengths of inner strap carry the tension load, a single length of an inner strap is used.

Figure 8:
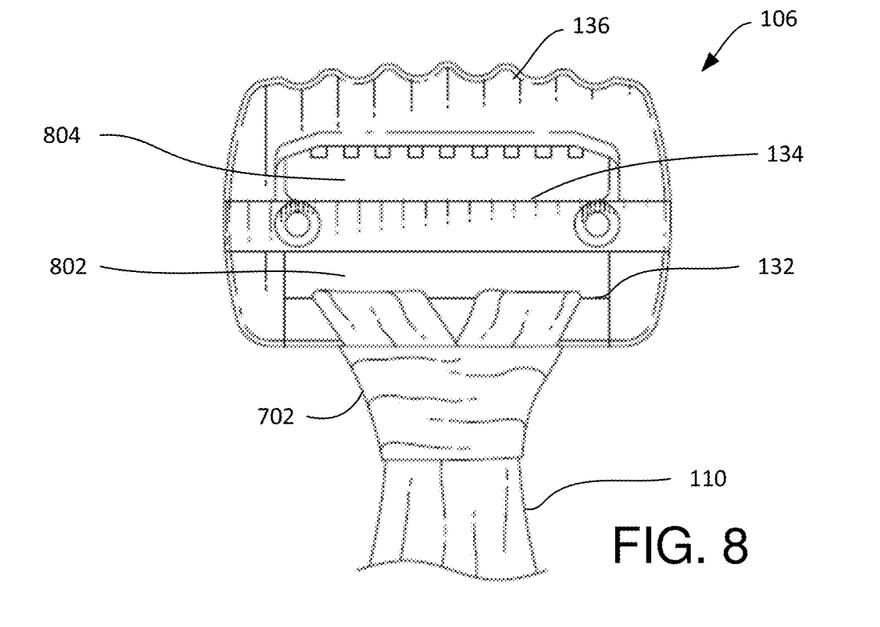
FIG. 8 is a top view showing the inner strap attached to the buckle with the outer strap removed.
Figure 9:
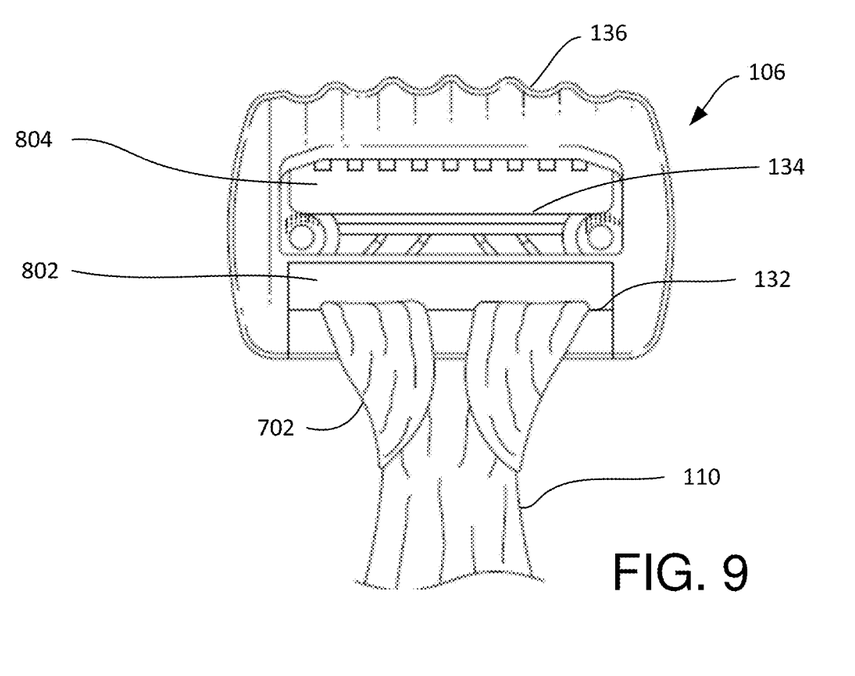
FIG. 9 is a bottom view showing the inner strap attached to the buckle with the outer strap removed.

FIGS. 8 and 9 show, respectively, a top view and a bottom view, of inner strap 110 at buckle 106, with outer strap 112 removed. FIGS. 8 and 9 show a gap 802 between rear crossbar 132 and center cross bar 134, and a gap 804 between center cross bar 134 and front cross bar 136. Inner strap 110 is knotted around rear cross bar 132. Two portions of inner strap 110 extend through gap 802 to wrap around rear cross bar 132 to form cow hitch knot 702.

To apply the tourniquet 100 to a limb, the user wraps the tourniquet around the subject appendage, loops the first end 102 through opening 804 of buckle 106, pulls the tourniquet 100 reasonably tight, and secures outer strap to itself using the hook and loop fasteners 204. The tourniquet is then tightened by twisting windlass 116, and after it is tight, securing windlass 116 in windlass clip 122 to prevent it from unwinding. Strap 126 with hook and loop fasteners is secured over the opening of windlass clip to ensure that windlass 116 stays in windlass clip 122.

Although the present invention and its advantages have been described in detail. For example, rather than inner strap 110 extending through slot 114, inner strap can be connected to windlass 116 in other ways, such as by looping over the windlass. While FIG. 5 shows both ends of the inner strap 110 secured to the outer strap at the same place spaced away from the second end of the tourniquet, the two ends could be secured at different places spaced away from the second send.

it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

I claim:

1. A tourniquet having a first end and a second end, comprising:
an outer strap;
an inner strap surrounded over a portion of its length by the outer strap;
a windlass having a slot, a portion of the inner strap that is not surrounded by the outer strap running through the slot; and
a buckle positioned at the first end;
in which the inner strap is secured to a portion of the buckle using a knot, such that there is no gap between the portion of the buckle and the knotted inner strap, and the inner strap is secured to the outer strap at a position spaced away from the second end.

2. A tourniquet having a first end and a second end, comprising:
an outer strap;
an inner strap surrounded over a portion of its length by the outer strap;
a windlass having a slot, a portion of the inner strap that is not surrounded by the outer strap running through the slot; and
a buckle positioned at the first end;
in which the inner strap extends to the buckle and is secured to the outer strap at a position spaced away from the second end.

3. The tourniquet of claim 2 in which the inner strap is knotted around a portion of the buckle using a slip knot.

4. The tourniquet of claim 2 in which the inner strap extends from the position spaced away from the second end, is knotted around a portion of the buckle, and extends back to the position spaced away from the second end.

5. The tourniquet of claim 2 in which the outer strap comprises a first side and a second side, the first side covered at least in part with at least one component of a hook and loop fastener.

6. The tourniquet of claim 5 in which one end of the outer strap is attached to a portion of the buckle and the other end of outer strap is configured to extend around a limb and through a slit in the buckle, and to attach via the at least one component of the hook and loop fastener to a portion of the outer strap.

7. The tourniquet of claim 2 in which the inner strap is secured to the outer strap by stitching that runs transverse to the length of the inner strap.

8. The tourniquet of claim 2 further comprising a thumb hole in the outer strap, the inner strap extending from the buckle and being secured to the outer strap on the side of the thumb hole opposite to the second end.

9. The tourniquet of claim 2 in which the inner strap is secured to the outer strap at a position spaced away by at least one half inch from the second end.

10. The tourniquet of claim 2 in which the inner strap is secured to the outer strap at a position that is spaced away by at least one inch from the second end.

11. The tourniquet of claim 2 in which the inner strap extends from the buckle to a position that is spaced away by at least two inches from the second end.

12. The tourniquet of claim 2, further comprising a windlass clip platform, the inner strap being positioned within the outer strap from the end of the windlass platform closest to the second end to the position spaced away from the second end.

13. The tourniquet of claim 2 further comprising a windlass platform, the windlass platform having a first set of slits and a second set of slits for passage of the inner strap and/or the outer strap.

14. The tourniquet of claim 13 in which the windlass platform supports on its top side a windlass clip.

15. The tourniquet of claim 13 in which the windlass is positioned above the windlass platform between the first set of slits and the second sets of slits.

16. A tourniquet having a first end and a second end, comprising:
an outer strap;
an inner strap surrounded over a portion of its length by the outer strap;
a windlass having a slot, a portion of the inner strap that is not surrounded by the outer-strap running through the slit;
a buckle positioned at the first end; and
in which the inner strap is knotted to a portion of the buckle.

17. The tourniquet of claim 16 in which the inner strap is knotted to a portion of the buckle such that there is no gap between the inner strap and the buckle at the knot.

18. The tourniquet of claim 16 in which the inner strap is knotted to a portion of the buckle using a slip knot.

19. The tourniquet of claim 18 in which the inner strap is knotted to a portion of the buckle using a cow hitch.

20. The tourniquet of claim 16 further comprising a windlass platform having for passage of the inner strap and/or the outer strap a first set of slits separated by a first cross bar and a second set of slits separated by a second cross bar.

21. The tourniquet of claim 20 in which the windlass is positioned above the windlass platform between the first set of slits and the second sets of slits.

22. The tourniquet of claim 20 in which the inner strap is routed from the top side of the windlass platform through the first slit of the first set of slits, under the first cross portion, and back to the top side of the windlass platform through the second slit of the first set of slits, through the windless, down through the first slit in the second set of lists, under the second cross bar, and up through the second slit of the second set of slits.

* * * * *